US007239915B2

(12) United States Patent
Cohen

(10) Patent No.: US 7,239,915 B2
(45) Date of Patent: Jul. 3, 2007

(54) HEMODYNAMIC OPTIMIZATION SYSTEM FOR BIVENTRICULAR IMPLANTS

(75) Inventor: Todd J. Cohen, Port Washington, NY (US)

(73) Assignee: Medtronic, Inc., Minneapolis, MN (US)

( * ) Notice: Subject to any disclaimer, the term of this patent is extended or adjusted under 35 U.S.C. 154(b) by 238 days.

(21) Appl. No.: 10/989,841

(22) Filed: Nov. 16, 2004

(65) Prior Publication Data

US 2005/0131469 A1 Jun. 16, 2005

Related U.S. Application Data

(60) Provisional application No. 60/530,072, filed on Dec. 16, 2003.

(51) Int. Cl.
*A61N 1/00* (2006.01)
(52) U.S. Cl. ....................................................... 607/17
(58) Field of Classification Search ................ 607/9–28
See application file for complete search history.

(56) References Cited

U.S. PATENT DOCUMENTS

| | | | |
|---|---|---|---|
| 3,614,954 A | 10/1971 | Mirowski et al. | |
| 3,614,955 A | 10/1971 | Mirowski et al. | |
| 3,716,059 A | 2/1973 | Welborn et al. | |
| RE27,652 E | 5/1973 | Mirowski et al. | |
| 3,866,615 A | 2/1975 | Hewson | |
| 3,878,564 A | 4/1975 | Yao et al. | |
| 3,942,536 A | 3/1976 | Mirowski et al. | |
| 4,164,946 A | 8/1979 | Langer | |
| 4,184,493 A | 1/1980 | Langer et al. | |
| 4,197,854 A | 4/1980 | Kasa | |
| 4,202,340 A | 5/1980 | Langer et al. | |
| 4,210,149 A | 7/1980 | Heilman et al. | |
| 4,223,678 A | 9/1980 | Langer et al. | |

(Continued)

OTHER PUBLICATIONS

Mirowski et al., "Recent Clinical Experience with the Automatic Implantable Cardioverter-Defibrillator"; Medical Instrumentation, vol. 20, 1986, pp. 285-291.

(Continued)

*Primary Examiner*—George Manuel
(74) *Attorney, Agent, or Firm*—Paul H. McDowall; Girma Wolde-Michael

(57) ABSTRACT

A system for monitoring a patient and treating the malfunctioning heart of the patient, either in an automatic mode or in a semiautomatic mode, includes means which derive at least one physiologic signal from or related to the patient's circulatory system representative of hemodynamic status. A feedback loop is implemented in a biventricular implant, in order to automatically or selectively optimize the patient's clinical hemodynamic status. Accordingly, the biventricular implant will be programmed to go through a series of AV delay, RV-LV timing and heart rate sequences which scan a preselected range of programmable values and apply those values to the patient's heart. Hemodynamic patient measurements will be recorded and preferably graphed over those applied values. The optimal AV delay, RV-LV timing sequence and pacing rate can then be selected either manually by a technician, physician or other operator, or automatically via the implant in order to secure the best personalized timing sequence for the patient. Preferably, the implant will also be capable of automatically recording hemodynamic information and adjusting intervals, in order to optimize hemodynamics without third party intervention. Also preferably, the automatic adjusting feature can be selectively programmed on or off using the device programmer, to control manual or automatic intervention.

33 Claims, 3 Drawing Sheets

U.S. PATENT DOCUMENTS

| | | |
|---|---|---|
| 4,254,775 A | 3/1981 | Langer |
| 4,291,699 A | 9/1981 | Geddes et al. |
| 4,295,474 A | 10/1981 | Fischell |
| 4,300,567 A | 11/1981 | Kolenik et al. |
| 4,303,075 A | 12/1981 | Heilman et al. |
| 4,316,472 A | 2/1982 | Mirowski et al. |
| 4,323,075 A | 4/1982 | Langer |
| 4,393,877 A | 7/1983 | Imran et al. |
| 4,403,614 A | 9/1983 | Engle et al. |
| 4,407,288 A | 10/1983 | Langer et al. |
| 4,427,011 A | 1/1984 | Spurrell et al. |
| 4,440,172 A | 4/1984 | Langer |
| 4,467,807 A | 8/1984 | Bornzin |
| 4,475,551 A | 10/1984 | Langer et al. |
| 4,523,595 A | 6/1985 | Zibell |
| 4,535,774 A | 8/1985 | Olson |
| 4,548,203 A | 10/1985 | Tacker, Jr. et al. |
| 4,548,209 A | 10/1985 | Wielders et al. |
| 4,559,946 A | 12/1985 | Mower |
| 4,562,846 A | 1/1986 | Cox et al. |
| 4,572,191 A | 2/1986 | Mirowski et al. |
| 4,576,170 A | 3/1986 | Bradley et al. |
| 4,592,367 A | 6/1986 | Imran |
| 4,603,705 A | 8/1986 | Speicher et al. |
| 4,614,192 A | 9/1986 | Imran et al. |
| 4,625,730 A | 12/1986 | Fountain et al. |
| 4,640,298 A | 2/1987 | Pless et al. |
| 4,662,377 A | 5/1987 | Heilman et al. |
| 4,693,253 A | 9/1987 | Adams |
| 4,708,143 A | 11/1987 | Schroeppel |
| 4,730,389 A | 3/1988 | Baudino |
| 4,730,619 A | 3/1988 | Koning et al. |
| 4,733,667 A | 3/1988 | Olive et al. |
| 4,763,655 A | 8/1988 | Wirtzfeld et al. |
| 4,770,177 A | 9/1988 | Schroeppel |
| 4,774,950 A | 10/1988 | Cohen |
| 4,785,812 A | 11/1988 | Pihl et al. |
| 4,799,493 A | 1/1989 | DuFault |
| 4,802,481 A | 2/1989 | Schroeppel |
| 4,803,987 A | 2/1989 | Calfee et al. |
| 4,819,662 A | 4/1989 | Heil, Jr. et al. |
| 4,830,006 A | 5/1989 | Haluska et al. |
| 4,846,195 A | 7/1989 | Alt |
| 4,865,036 A | 9/1989 | Chirife |
| 4,867,160 A | 9/1989 | Schaldach |
| 4,867,161 A | 9/1989 | Schaldach |
| 4,869,252 A | 9/1989 | Gilli |
| 4,870,341 A | 9/1989 | Pihl et al. |
| 4,870,968 A | 10/1989 | Wiertzfeld et al. |
| 4,873,980 A | 10/1989 | Schaldach |
| 4,895,151 A | 1/1990 | Grevis et al. |
| 4,899,751 A | 2/1990 | Cohen |
| 4,899,752 A | 2/1990 | Cohen |
| 4,917,115 A | 4/1990 | Flammang et al. |
| 4,919,147 A | 4/1990 | Reinhardt et al. |
| 4,928,688 A | 5/1990 | Mower |
| 4,940,052 A | 7/1990 | Mann et al. |
| 4,960,133 A | 10/1990 | Hewson |
| 4,967,748 A | 11/1990 | Cohen |
| 4,967,749 A | 11/1990 | Cohen |
| 4,972,834 A | 11/1990 | Begemann et al. |
| 4,984,572 A | 1/1991 | Cohen |
| 4,986,270 A | 1/1991 | Cohen |
| 5,002,052 A | 3/1991 | Haluska |
| 5,003,991 A | 4/1991 | Takamaya et al. |
| 5,005,574 A | 4/1991 | Fearnot et al. |
| 5,014,698 A | 5/1991 | Cohen |
| 5,027,816 A | 7/1991 | Cohen |
| 5,036,848 A | 8/1991 | Hewson |
| 5,054,485 A | 10/1991 | Cohen |
| 5,085,213 A | 2/1992 | Cohen |
| 5,097,830 A | 3/1992 | Eikefjord et al. |
| 5,097,831 A | 3/1992 | Lekholm |
| 5,119,813 A | 6/1992 | Cohen |
| 5,156,148 A | 10/1992 | Cohen |
| 5,163,429 A | 11/1992 | Cohen |
| 5,178,149 A | 1/1993 | Imburgia et al. |
| 5,179,952 A | 1/1993 | Buinevicius et al. |
| 5,191,885 A | 3/1993 | Bilof et al. |
| 5,265,623 A | 11/1993 | Kroll et al. |
| 5,269,301 A | 12/1993 | Cohen |
| 5,330,505 A | 7/1994 | Cohen |
| 5,417,713 A | 5/1995 | Cohen |
| 5,584,868 A | 12/1996 | Salo et al. |
| 5,836,987 A | 11/1998 | Baumann et al. |
| 6,238,420 B1 | 5/2001 | Bakels et al. |
| 6,512,953 B2 * | 1/2003 | Florio et al. ............... 607/28 |
| 6,567,700 B1 | 5/2003 | Turcott et al. |
| 6,597,951 B2 | 7/2003 | Kramer et al. |
| 6,606,516 B2 | 8/2003 | Levine |
| 2001/0031993 A1 | 10/2001 | Salo et al. |
| 2002/0151938 A1 | 10/2002 | Corbucci |
| 2003/0018363 A1 | 1/2003 | Ding et al. |
| 2003/0060851 A1 | 3/2003 | Kramer et al. |
| 2003/0083700 A1 | 5/2003 | Hill |
| 2003/0100925 A1 | 5/2003 | Pape et al. |
| 2003/0130702 A1 | 7/2003 | Kramer et al. |
| 2003/0144703 A1 | 7/2003 | Yu et al. |
| 2003/0199936 A1 | 10/2003 | Struble et al. |
| 2003/0204212 A1 | 10/2003 | Burnes et al. |
| 2004/0147969 A1 * | 7/2004 | Mann et al. ............... 607/17 |

OTHER PUBLICATIONS

Mirowski, "The Automatic Implantable Cardioverter-Defibrillator: An Overview"; JACC, vol. 6, No. 2, Aug. 1985, pp. 461-466.

Cohen et al., "A Universal Microprocessor Controlled Heart Rhythm Control System"; Annual International Conference of IEEE Engineering in Medicine and Biology Society, vol. 13, No. 2, 1991.

Cohen et al., "Mixed Venous Oxygen Saturation for Differentiating Stable from Unstable Tachycardias"; American Heart Journal, vol. 122, No. 3, Sep. 1991, pp. 733-740.

Cohen, "A Theoretical Right Atrial Pressure Feedback Heart Rate Control System to Restore Physiologic Control to the Rate-limited Heart"; PACE, vol. 7, Jul.-Aug. 1984.

Cohen et al., "Hemodynamic Responses to Rapid Pacing: A Model for Tachycardia Differentiation"; PACE, vol. 11, Nov. 1988, Part I.

Cohen et al., "A Hemodynamically Response Antitachycardia System: Theoretical Basis for Design"; Journal of Electrophysiology, vol. 2, No. 4, 1988.

Cohen et al., "A Hemodynamically Responsive Antitachycardia System—Development and Basis for Design in Humans"; Presented at the 11th Annual Scientific Session of the North American Society of Pacing and Electrophysiology, San Diego, May 31-Jun. 2, 1990..

Cohen et al., "Biosensor Application to Antitachycardia Devices"; PACE, vol. 14, Feb. 1991, Part II.

Aubert et al., "Automatic Defibrillator, Antitachy Pacemaker and Cardioverter"; IEEE, 8th Annual Conference of the Engineering in Medicine and Biology Society, 1986, pp. 239 and 240.

Vervydt et al., "Automatic Defibrillator, Antitachy Pacemaker and Cardioverter"; 1986 Computers in Cardiology Conference, Boston Mass., 1987, pp. 45-48.

* cited by examiner

HEMODYNAMIC OPTIMIZATION SYSTEM FOR BIVENTRICULAR IMPLANTS

CROSS REFERENCE TO RELATED APPLICATIONS

This application claims priority to U.S. provisional patent application Ser. No. 60/530,072, filed Dec. 16, 2003 and naming the present inventor, the contents which are incorporated herein by reference in its entirety.

BACKGROUND OF THE INVENTION

1. Field of the Invention

This invention pertains generally to biventricular implants, and more specifically to methods of operating those implants in order to manually, semi-automatically, or automatically optimize their operation.

2. Description of the Related Art

Deaths from cardiovascular diseases ("CVD") is a very serious problem in the United States and throughout the world. Since 1900, CVD has been the No. 1 killer in the United States for every year (except for 1918).

The CDC estimates that each year around 400,000 people die of heart disease in an emergency department or before reaching a hospital; this accounts for a very large percentage of all cardiac deaths. A significant number of these deaths are not first events, but subsequent to first diagnosis and treatment of CVD. Consequently, there is much impetus to developing improved techniques for the care and management of CVD.

One such approach of recent vintage has been the integration of electrical and electronic devices into the care and management of CVD. As is evident in modern society, electronic devices have become ubiquitous. Everywhere we travel, we do so with the assistance and convenience afforded by these microminiaturized wonders. Watches, personal digital assistants, laptop computers, and cellular telephones are all recognizable and commonplace devices carried about by persons. However, as technology has permitted, these devices are not the only ones which may be carried with a person.

Many modern microelectronic devices are integrated or concealed within other devices or even within people. Pacemakers, hearing aids, automatic medication dispensers, bone growth stimulators, biological recorders and alarms, and even personal safety and alerting devices have become very prevalent within, on, or transported by people. It is extremely commonplace for many mechanical and even chemical devices to additionally include microelectronic devices, the electronics performing such diverse roles as timers, monitors, sensors, controls and a myriad of other functions. These functions may simply be more economical than a mechanical or chemical counterpart, but will often provide functions that would otherwise be impractical or impossible to achieve.

In recent years, substantial progress has been made in pacemakers and in the development of cardioverting and defibrillating techniques for effectively treating various heart disorders and arrhythmias. Past efforts have resulted in the development of implantable electronic pacemakers and standby cardioverters-defibrillators which, in response to the detection of an abnormal cardiac rhythm, discharge sufficient energy via electrodes connected to the heart to depolarize and restore it to normal cardiac rhythm. An early example of this cardioverting and defibrillating technique is disclosed in U.S. Pat. No. 3,942,536 of Mirowski et al, the teachings which are incorporated herein by reference. The Mirowski et al technique involves responses to a sensed peak right ventricular systolic pressure dropping below a fixed predetermined level and not returning above the predetermined level for a given period of time.

Efforts have also been directed toward developing techniques for reliably monitoring heart activity in order to determine whether cardioversion and defibrillation are desirable or necessary. Such techniques include monitoring ventricular rate or determining the presence of fibrillation on the basis of the probability density function (PDF) of an electrocardiographic signal. A system using the PDF technique statistically compares the location of points of a cardiac waveform with the expected locations of points of the normal waveform. When the waveform becomes irregular, as measured by its probability density function, an abnormal cardiac function is suggested. The latter technique is described in U.S. Pat. Nos. 4,184,493 and 4,202,340, both by Langer et al, the teachings which are incorporated herein by reference. In the Langer et al U.S. Pat. No. 4,202,340, probability density function is defined as "the fraction of time, on the average, that a given signal spends between two amplitude limits." It has been noted that the probability density of an ECG changes markedly between ventricular fibrillation and normal cardiac rhythm. Accordingly, VF can be detected by providing a mechanism for generating a probability density function, or portion thereof, or approximately one or more points on the function. The entire probability density function need not always be developed; rather, it is sometimes sufficient to develop only particular values of the function at certain sampling points.

A more recent system, as disclosed in U.S. Pat. No. 4,475,551 of Langer et al and also incorporated herein by reference, utilizes both the PDF technique to determine the presence of an abnormal cardiac rhythm and a heart rate sensing circuit for distinguishing between ventricular fibrillation and high rate tachycardia (the latter being indicated by a heart rate above a predetermined minimum threshold), on the one hand, and normal sinus rhythm or a low rate tachycardia (indicated by a heart rate falling below a predetermined minimum threshold), on the other hand.

Still further research in this area has resulted in the development of a heart rate detector system which accurately measures heart rate from a variety of different electrocardiogram (ECG) signal shapes. One such system is disclosed in U.S. Pat. No. 4,393,877 of Imran et al, the teachings which are also incorporated herein by reference.

An apparatus and method for treating tachyarrhythmias wherein the presence of a patient tachyarrhythmia is detected and a first anti-tachyarrhythmia therapy (anti-tachycardia pacing) is given at a first energy level has been proposed in U.S. Pat. No. 4,895,151 by Grevis et al, the teachings which are incorporated herein by reference. The hemodynamic condition of the patient is measured and a length of time to therapy switchover is continually derived during the application of the first anti-tachyarrhythmia therapy. The length of time to switchover is a function of the hemodynamic condition of the patient. When the time following detection of the patient tachyarrhythmia exceeds the length of time to switchover, a second anti-tachyarrhythmia therapy (a high energy shock) at a second energy level is provided. The average cardiac cycle length may be used as an indicator of the hemodynamic condition. Only a single hemodynamic parameter is utilized, at one time, in the Grevis et al apparatus, cardiac cycle length being the parameter illustrated.

An implantable cardiac stimulator that integrates the functions of bradycardia and anti-tachycardia pacing-type therapies, and cardioversion and defibrillation shock-type therapies, is disclosed in U.S. Pat. No. 4,830,006 of Haluska et al, the teachings which are incorporated herein by reference. The stimulator is programmable to provide a multiplicity of hierarchical detection algorithms and therapeutic modalities to detect and treat classes of ventricular tachycardia according to position within rate range classes into which the heart rate continuum is partitioned, and thus according to hemodynamic tolerance, with backup capabilities of defibrillation and bradycardia pacing at the higher and lower regions of the rate continuum outside the range of the ventricular tachycardia classes. Aggressiveness of the therapy is increased with elapsed time and increasing heart rate and detection criteria are relaxed with increasing heart rate and thus with increasing hemodynamic intolerance of the tachycardia.

A method for detecting and treating ventricular tachyarrhythmias of a patient's heart is disclosed in U.S. Pat. No. 5,002,052 of Haluska, the teachings which are incorporated herein by reference, which includes the steps of selectively dividing the heart rate continuum into regions including at least two classes of tachycardia, contiguous to each other and of progressively higher heart rate ranges, the lowest and highest of the tachycardia classes being bounded respectively by a sinus rate region and a fibrillation region of the continuum. The boundaries between the tachycardia classes and between the lowest and highest of those classes are selectively adjusted and the respective sinus rate and fibrillation regions to correspondingly adjust the rate ranges of the classes selectively detecting cardiac events anywhere within the continuum and distinguishing between normal and abnormal tachycardias. Treating a detected abnormal tachycardia with any of a multiplicity of therapy regimens of differing degrees of aggressiveness, toward terminating the detected tachycardia is proposed.

A process and apparatus for patient danger recognition and forecasting, particularly for the intensive medical care of the patient has been proposed in U.S. Pat. No. 4,197,854 to Kasa, the teachings which are incorporated herein by reference. The Kasa invention uses various variables to set up a danger function that represents the probability of occurrence of a danger condition, forms average values of the danger function throughout subsequent time periods that are shorter than the time required for a medical intervention. Formed average values with levels of increasing sequences of threshold values are compared providing an indication associated with the highest exceeded threshold value. The average values are used to set up a regression function which approximates the sequence thereof. A subsequent extrapolated value of the function is determined for the next time period that represents a forecast average value of the danger function. The extrapolated value is indicated, provided it is higher than a predetermined level. Preferably three threshold values are used in the comparing step, with magnitudes of 40, 60 and 80% of the danger function, respectively.

U.S. Pat. No. 4,770,177 of Schroeppel, the teachings which are incorporated herein by reference, discloses a pacer which paces a heart in accordance with the heart pacer rate needed to produce a required cardiac output while a person is exercising or undergoes emotional stress, in response to changes in venous blood vessel diameter. The pacer is adapted to be implanted in a human body and has a pulse generator and control circuitry, which may be realized by a microprocessor. A pacing lead adapted to be implanted in a heart has a tip electrode adapted to engage and supply pacing pulses to a right ventricle of a heart. A piezoelectric sensor determines changes in a diameter of a vein in the human body. Computing circuitry, including the control circuitry, relates the changes in venous blood vessel diameter with the required pacing rate needed to supply a desired cardiac output, and causes the pacer to pace the heart at the required rate when the heart is not naturally paced. The pacer of Schroeppel is not combined with any cardioverter and defibrillator.

Currently anti-tachycardia systems detect arrhythmias primarily by sensing rate and perform inadequately in the differentiation of hemodynamically stable from unstable rhythms. These devices, for example, may fire during a stable supraventricular tachycardia (SVT), inflicting pain and wasting energy. Damage to the heart may result.

A commonly used implantable anti-tachycardia device is the automatic implantable cardioverter and defibrillator which is commercially available. These devices continuously monitor myocardial electrical activity, detecting ventricular tachycardia (VT) and ventricular fibrillation (VF), and delivering a shock to the myocardium to terminate the arrhythmia. This cardioverter and defibrillator has been shown to reduce the mortality rate in patients with malignant arrhythmias with initial studies at Johns Hopkins Hospital and Stanford Medical Center demonstrating a 50 percent decrease in the anticipated total incidence of death, as reported by Mirowski et al, "Recent Clinical Experience with the Automatic Implantable Cardioverter-Defibrillator, Medical Instrumentation, Vol. 20, pages 285–291 (1986). Arrhythmias are detected by (1) a rate ® wave) sensor and (2) the probability density function (PDF) of an EKG signal which defines the fraction of time spent by the differentiated electrocardiogram between two amplitude limits located near zero potential. Presently, the functional window of the PDF is wide to permit the detection of both VT and VF, and therefore, this device functions essentially as a rate-only sensing system. As reported by Mirowski, "The Automatic Implantable Cardioverter-Defibrillator: An Overview", JACC, Vol. 6, No. 2, pages 461–466, (August, 1985), when an arrhythmia fulfills either the rate or PDF criteria, the device delivers Schuder's truncated exponential pulse of 25 Joules some 17 seconds after the onset of the arrhythmia. The device can recycle as many as three times if the previous discharge is ineffective with the strength of the second, third and fourth pulses being increased to 30 Joules. After the fourth discharge, approximately 35 seconds of nonfibrillating rhythm are required to reset the device.

Closed loop intravenous drug delivery systems have been developed and are undergoing evaluation for the treatment of heart failure. Such systems may also be incorporated into an implantable device to permit the delivery of electrical therapy (pacing/cardioversion/defibrillation) as well as drug therapy, to correct a malfunctioning heart.

In addition to the standard automatic implantable cardioverter and defibrillator characterized by the above-noted dual detection algorithm, a variant of the device which features a sensing system that relies only on the analysis of heart rate is also available. This "rate-only" version of the known cardioverter and defibrillator preferred by some investigators, is more sensitive than the dual detection version unit and theoretically less likely to miss ventricular tachycardias with narrow QRS complexes. It is believed that the "rate-only" system, on the other hand, may be too sensitive, delivering cardioverting and defibrillating pulses too often or too soon, no hemodynamic parameter having been taken into consideration.

One drawback with many current systems is that they function primarily as a rate-only or single-hemodynamic-parameter driven systems and may fire for nonmalignant as well as malignant tachycardias. These firings are not benign; potentially endangering myocardium, wasting energy and inflicting pain on the conscious patient, all distinct shortcomings and disadvantages. Furthermore, these devices operate in a single mode; that is, such systems apply therapy, such as cardioverting and defibrillating pulses to the myocardium automatically, without the option or opportunity for confirmation or intervention by medical personnel.

External ST segment monitoring systems are also commercially available. These systems compare the normal or baseline ST segment of an ECG to that during normal exercise or activity to determine whether the change is significant and indicative of ischemia. Such monitoring systems are currently worn on the patient's waist or over the shoulders, and no active treatment is offered, since ischemia is only identified after the recording is complete, and the tape is scanned. It is possible that this information can be acquired in real time, such that appropriate drug therapy could be delivered to correct the ischemia.

The present inventor has developed practical systems and methods designed to in large measure overcome or ameliorate the deficiencies of the prior art. These patents, the teachings of each which are incorporated herein by reference, include U.S. Pat. Nos. 4,774,950; 4,899,751; 4,899,752; 4,967,748; 4,967,749; 4,984,572; 4,986,270; 5,014,698; 5,027,816; 5,054,485; 5,085,213; 5,119,813; 5,156,148; 5,163,429; 5,269,301; 5,330,505; and 5,417,713.

As but one example, a system for and method of treating a malfunctioning heart based on hemodynamics at a single site in a circulatory system was the subject of above referenced U.S. Pat. No. 4,774,950 by the present inventor and granted Oct. 4, 1988. Therein, the dynamics of mean arterial pressure (MAP) mean right atrial pressure (MRAP), mean right ventrical pressure (MRVP), mean left atrial pressure (MLAP), mean left ventrical pressure (MLVP) or mean central venous pressure (MCVP) were respectively proposed as the single-site or single-parameter basis for cardioversion and defibrillation, and both apparatus and method were disclosed. These aforementioned patents also disclose the incorporation of pharmacological therapies in further combination with cardioversion and defibrillation. As disclosed for exemplary purposes in U.S. Pat. No. 5,014,698 by the present inventor, the malfunction correcting circuits will produce malfunction correcting electrical output signals, which are delivered to the patient as required. Among these are signals which in turn control drug delivery devices, which may consist of a number of pumps or other drug delivery devices, such as gravity operated delivery systems supply medications to the patient in an effort to overcome or correct the malfunction. These output signals and/or drug(s) and/or the pumping assist are provided to effect termination of, or at least treat in an effective manner, singly or in combination stable SVT, unstable SVT, stable VT, unstable VT, stable atrial fibrillation, unstable atrial fibrillation, ventricular fibrillation, asystole, stable bradycardia, unstable bradycardia, ischemia, early infarction and both stable and unstable heart failure.

Although pharmacological and pacer therapy have ameliorated symptoms and improved the survival of patients with chronic heart failure (CHF) and other cardiovascular disorders, CHF remains a progressive disease causing incremental morbidity and early mortality. More recently, the results of the COMPANION trial demonstrated improved mortality and hospitalization in patients with heart failure who have an intraventricular conduction delay, through cardiac resynchronization achieved with atrial-synchronized biventricular pacing. Left bundle branch block in structurally normal hearts results in loss of synchrony of ventricular contraction and impairs both regional and global left ventricular systolic function. In hearts with good overall left ventricular systolic function this has very little clinical effect. But in patients with ischemic or idiopathic dilated cardiomyopathy it further impairs already poor systolic function and may have a major clinical impact. The prevalence of conduction delay in patients with heart failure has recently been estimated to approach 30%, and this has led to rapid development of biventricular pacing in an attempt to restore synchronous ventricular contraction and so improve left ventricular function. As an added benefit, based upon further recent studies, cardiac resynchronization seems to reduce the risk of clinical deterioration during follow up, with the combined risk of a major clinical event, defined as death or admission for worsening heart failure, being reduced by 40%. The number of patients requiring admission for heart failure also appear to involve a reduced number of total hospital days for management of heart failure.

Since the publication of the COMPANION results, there has been an exponential increase in biventricular cardioverter-defibrillator implants. These devices have a right atrial lead as well as a right and left ventricular lead. Two timing intervals, the atrioventricular (AV) delay and the RV to LV delay, can typically be manually programmed while measuring the patient's hemodynamic, either via echocardiography or via invasive hemodynamic monitoring or via transthoracic impedance. Exemplary of these devices and methods, and of varying relevance, are U.S. Pat. No. 5,584,868 by Salo et al; U.S. Pat. No. 5,836,987 by Baumann et al; U.S. Pat. No. 6,238,420 by Bakels et al; U.S. Pat. No. 6,567,700 to Turcott et al; U.S. Pat. No. 6,597,951 by Kramer et al; U.S. Pat. No. 6,606,516 by Levine; and U.S. published applications 2001/0031993 by Salo etal; 2002/0151938 by Corbucci; 2003/0018363 by Dinget al; 2003/0060851 by Kramer et al; 2003/0083700 by Hill; 2003/0100925 by Pape et al; 2003/0130702 by Kramer et al; 2003/0144703 by Yu et al; 2003/0199936 by Struble et al; and 2003/0204212 by Burnes et al, the teachings of each which are incorporated herein by reference.

As will be recognized from the substantial body of art incorporated herein above by reference, including numerous patents assigned to the present inventor and others, the electrical and mechanical arrangements necessary for the incorporation of technically advanced and flexible pacers and defibrillators is known in the art. However, successful implementation of the physical and electronic technologies for the ever broader effective clinical application has been somewhat more elusive. Among the various challenges faced are the varying underlying causes of a malfunctioning heart, the complexity of diagnosis and myriad of devices which may presently be required for appropriate application to a given root cause, the difficult set-up of these prior art devices for operation, and the risk of undesirable inappropriate functioning of the device.

SUMMARY OF THE INVENTION

The difficulties and drawbacks prevalent among prior art systems are, in the present invention, ameliorated by creating a feedback loop in a cardiac stimulator in order to automatically or selectively optimize atrioventricular delay, heart rate, and RV-LV timing sequence.

From one system perspective, the invention can be seen as a multi-mode system for monitoring a patient and treating a malfunctioning heart of the patient selectively in automatic and semiautomatic modes. In this system, means derive at least one physiological signal representative of a hemodynamic status of the patient. Output means provide at least one heart-malfunction-corrective output. Range controlling means limit upper and lower bounds for the heart-malfunction-corrective output. Scanning means vary delivery of the heart-malfunction-corrective output. Monitoring means record the at least one physiologic signal responsive to changes in delivery by the scanning means. A mode selection means operable by a human operator enables the output means to operate selectively in an automatic mode independent of the human operator and in a semiautomatic mode requiring confirmation by the human operator. Using this system, at least one malfunction of the heart may be treated selectively in automatic and semiautomatic modes.

From a second system perspective, the invention can be seen as a system for monitoring a patient and treating the malfunctioning heart of the patient through electrical signals generated by a biventricular pacemaker and coupled to the patient's heart. Means are provided for deriving at least one physiologic signal representative of the patient's hemodynamic status. Means are also provided for varying at least one of atrioventricular (AV) delay, right ventricular (RV) to left ventricular (LV) timing and heart rate of the electrical signals. A range of values are provided for each of the at least one of atrioventricular (AV) delay, right ventricular (RV) to left ventricular (LV) timing and heart rate. A feedback loop initiates the varying means to vary at least one of the AV delay, RV-LV timing and heart rate of the electrical signals through the provided range of values. A means applies the electrical signals varied through the range of values to the patient's heart. Recording means measures the varied electrical signals and physiologic signal responsive to the varied electrical signals. A means determines an optimum value from the range of values, responsive to the recording means and feedback loop. A means is provided to select at least one of an optimal AV delay, optimal RV-LV timing sequence and an optimal pacing rate to secure an optimized timing sequence for the patient.

In its apparatus aspect, the invention can be seen as a bi-ventricular cardioverter-defibrillator implant having a right atrial lead and a right and left ventricular lead, wherein two timing intervals including an atrioventricular (AV) delay and further including a right ventricular (RV) to left ventricular (LV) delay are provided. These timing intervals are manually programmed while measuring a hemodynamic parameter from the patient's circulatory system. According to the invention, the improvement comprises a feedback loop to optimize the timing signals on an automatic basis, thereby providing the best timing sequence to achieve optimal circulation for the specific patient, and thereby improving one or more of the patient's contractility, left ventricular ejection fraction and/or their symptoms, and thereby improving their overall quality of life.

In a method manifestation, the invention is a method for hemodynamic optimization of a biventricular implant. In accord with the inventive method, a right ventricle (RV) to left ventricle (LV) timing range is programmed to produce a programmed RV to LV timing range. An RV to LV timing sequence is varied discretely or continuously throughout the entire programmed RV to LV timing range. An optimal RV to LV timing sequence is determined responsive to the RV to LV timing sequence varying step. The biventricular implant is then set to the optimal RV to LV timing sequence.

OBJECTS OF THE INVENTION

The principle object of the present invention is to provide a multi-mode system for monitoring and semi-automatically or automatically optimizing circulation in a patient having a malfunctioning heart. Most preferably, in accord with this principle object, the present invention will decrease mortality, alleviate symptoms, and thereby improve overall quality of life.

A further object of the present invention is to provide a multi-mode system for monitoring a patient and for treating the malfunctioning heart of the patient, the system being optimally adjusted responsive to changes in at least one physiologic parameter, such as pressure(s) at one or more sites in the circulatory system of a patient, and to an electrical signal or signals derived from action of the heart and the present invention. For the purposes of the present disclosure, the term physiologic parameter means any parameter which is derived from the human body which relates information and reflects the hemodynamic state or condition of the patient. This term includes information which may be derived from a biosensor (or biosensors) or a characteristic of an electrical signal which relates hemodynamic information. An example would be the determination of ST signal changes from the electrical signal as a physiologic parameter which indicates ischemia.

Another object of the present invention is to enable the selective automatic or manual adjustment of the system. Yet another object of the present invention is to enable periodic automatic readjustment of the system.

BRIEF DESCRIPTION OF THE DRAWINGS

The foregoing and other objects, advantages, and novel features of the present invention can be understood and appreciated by reference to the following detailed description of the invention, taken in conjunction with the accompanying drawings, in which.

DESCRIPTION OF THE PREFERRED EMBODIMENT

As has been recited in the prior art and herein above, one of the more significant obstacles in the design and implementation of biventricular pacing devices has been the selection and control of optimum pacing delays. These delays are known to vary by patient, and in some instances, by patient position and activity. The preferred embodiment method 100 of the present invention, illustrated by flowchart in FIG. 1, overcomes the limitations of the prior art by implementing a feedback loop in a biventricular implant, in order to automatically or selectively optimize both the atrioventricular delay and the RV-LV timing sequence.

In order to optimize the patient's clinical hemodynamic status, the biventricular implant will be programmed in accord with method 100 to go through a series of AV delay and RV-LV timing and heart rates sequences which scan the range of programmable values and apply those values to the patient's heart. Hemodynamic patient measurements will be recorded and preferably graphed over those applied values. The optimal AV delay and RV-LV timing sequence and pacing rate can then be selected either manually or automatically via the device in order to secure the best personalized timing sequence for the patient. Preferably, the implant will also be capable of automatically recording hemodynamic information and adjusting intervals, in order to optimize hemodynamics without third party intervention. Also preferably, the automatic adjusting feature can be selectively programmed on or off using the device programmer, to control manual or automatic intervention.

Figure 1:
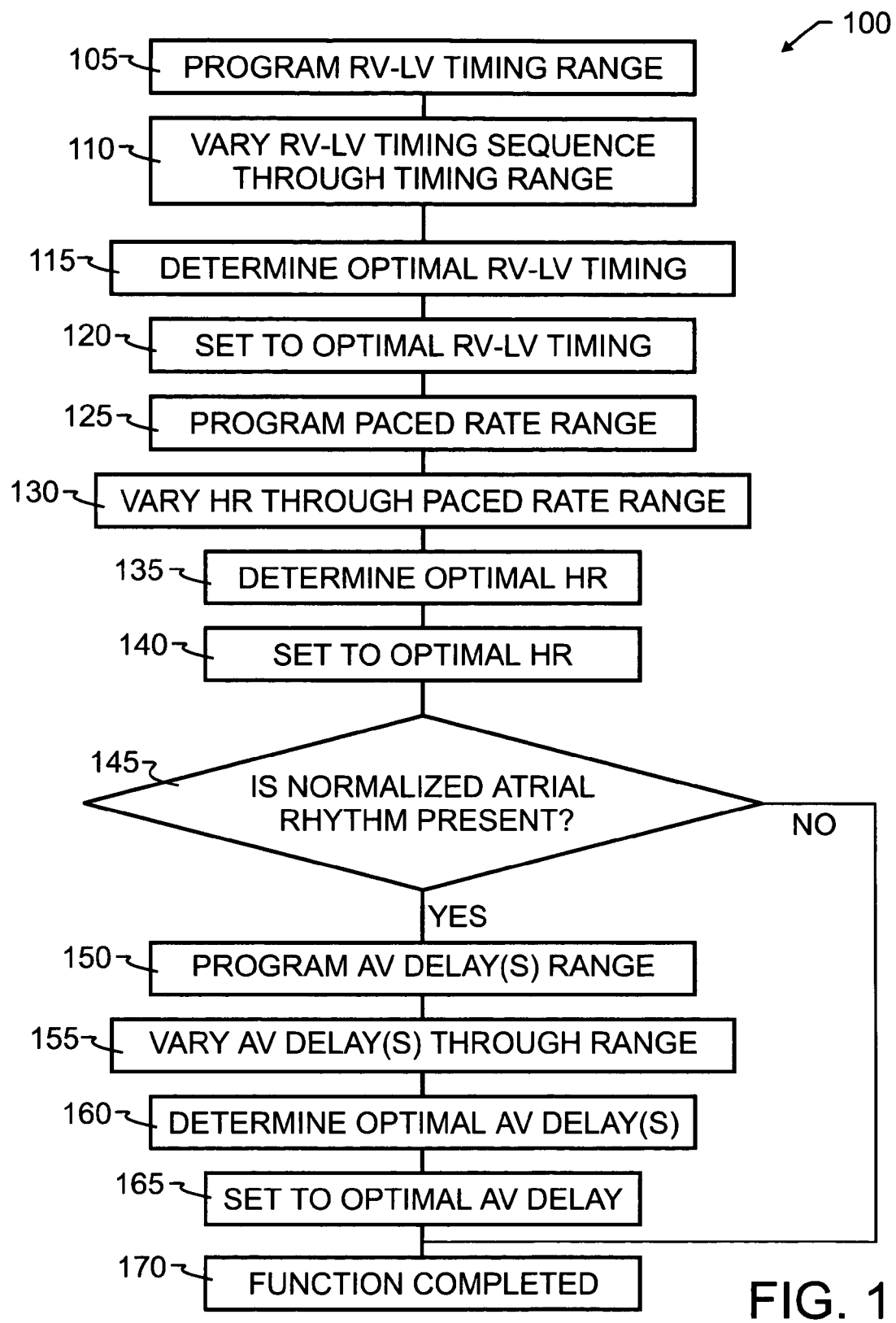
FIG. 1 illustrates a first preferred method of hemodynamic optimization for biventricular implants, designed in accord with the teachings of the present invention, by flow chart.

As illustrated in FIG. 1, at step 105, a Right Ventricle to Left Ventricle (RV-LV) delay time range suitable for, and preferably slightly more extensive than a particular patient's need is stored in the biventricular implant or associated controlling equipment. As should be apparent to those skilled in the art, there are a variety of implants, some which retain controlling operations entirely within the implant, and others that provide at least one type of either temporary or permanent communications link to a remote control panel or system. If controlling operations are retained within the implant, then the programming of the RV-LV range must be made either by temporary wired connection to the implant during implantation, by wireless connection, or by programming prior to implantation.

The biventricular implant is then stepped through the entire RV-LV delay time range that was selected in step 105, as illustrated by step 110, either continuously or at various discrete intervals. Where discrete intervals are used, these may be manually selected or automatically calculated by suitable programming. In response to the varying RV-LV delay times, which may include positive values (delays) or negative values (advances), the patient's hemodynamic output is anticipated to change. Electrical and hemodynamic information may be obtained from either or both of the pulse generator and device lead. Hemodynamic information can be gathered via impedance measures, QT interval, accelerometer, mixed venous oxygen saturation, cardiac output or similar marker, intracardiac pressure monitoring, blood pressure, temperature, and other suitable physiologic parameters. In addition, transthoracic impedance can be obtained via a separate device monitored by technician, physician or other programmer, who in turn may then provide feedback to the implanted system.

During the step 110 varying of the RV-LV delay range, throughout the delay time range programmed in step 105, hemodynamic output is recorded. This recording may once again depend upon the particular implant. It is anticipated herein that many modern implants, most which are equipped with microprocessor control, will have the ability to record hemodynamic output directly within memory provided with the microprocessor. However, the invention is not so limited, and remote recording is additionally contemplated herein. Further, the recording is not limited solely to electronic recording, and may include any other suitable technique which is desired. For exemplary purposes only, and not limiting the scope of the invention, other very diverse techniques such as paper tape recording or graphing are known in the industry.

Optimal RV-LV delay is then selected by the determination of the maximum hemodynamic output in step 115. This determination may be made automatically, using suitable logic to store each value and then find the maximum from the results. Otherwise, the results may be obtained automatically, but then displayed for a human operator to review and select from, yielding a semiautomatic optimization. In the preferred embodiment, the results may, in the semiautomatic approach, be graphed such as illustrated in FIG. 3.

Figure 3:
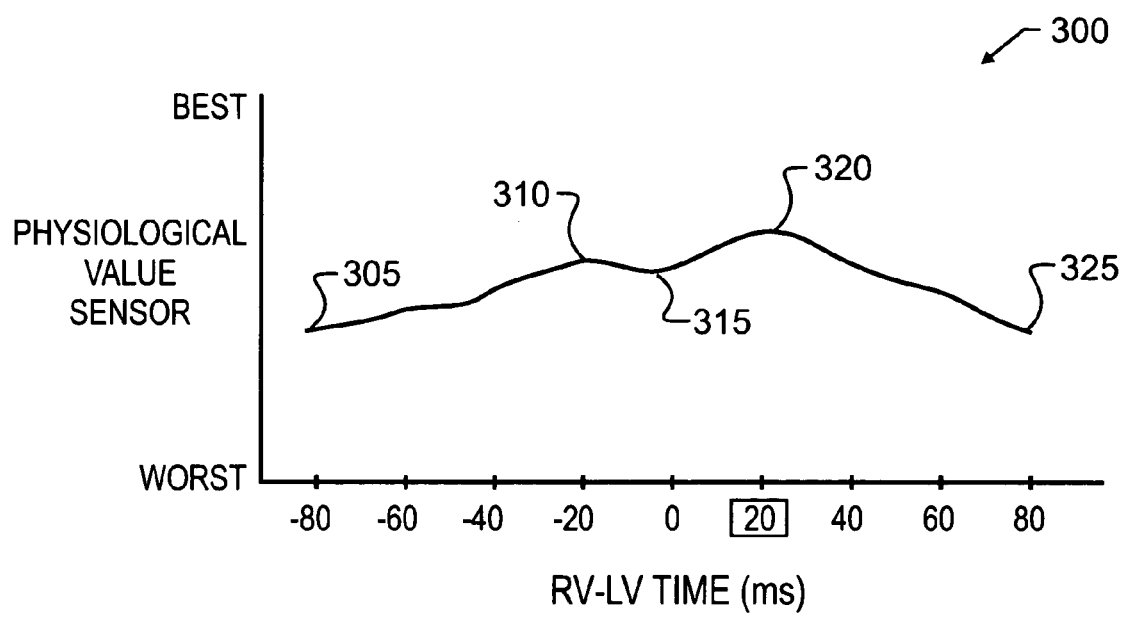
FIG. 3 illustrates an exemplary graph of RV-LV delay versus hemodynamic status as measured by suitable physiologic parameter.

As may become apparent upon a closer review of FIG. 3, there may be times where local maxima occur, but do not yield the overall maximum for a given range. As illustrated therein, prior art systems may typically start at one timing extreme or another on the abscissa, such as at −80 milliseconds in the figure. This delay of −80 milliseconds will yield a physiologic value corresponding to the ordinate shown by point 305, which represents relatively poorer hemodynamic performance than shown by points 310, 315 and 320. As the RV-LV delay is changed in the prior art from −80 milliseconds to −20 milliseconds, the hemodynamic value increases to a local maximum value 310. Since the changes immediately adjacent to local maximum value 310 in RV-LV delay time will result in reduced output, systems that only try to vary the interval on a continuous basis and try to determine optimized output from the immediately adjacent intervals will stop at point 310. Said another way, any system which fails to step through the entire range, and which starts at the far left end of RV-LV delay times as represented in FIG. 3, may not actually obtain the most optimum time delay but will instead be confused by local maxima such as point 310. However, in accord with the teachings of the present invention, the RV-LV delay interval will be varied through the entire range, and will thus pass beyond local minima 315 and into the maximal point 320. Since the full range will be tested, even point 325, which is associated with relatively poorer hemodynamic output, will be tested.

In the semi-automatic operating mode, this graph as shown in FIG. 3 may then be presented to or displayed for a physician or technician, who will then manually select point 320, corresponding to a 20 millisecond delay, as the most optimal delay. However, for various reasons the operator may instead use the information from a plot such as that illustrated in FIG. 3 to select a point different from 320, for exemplary purposes to improve overall hemodynamic performance in combination with other pacer delays and rates, or to factor in other medical information about a patient that is not evident from FIG. 3.

Once the optimal RV-LV delay timing has been determined, this value will be set within the biventricular implant, as illustrated by step 120. This may be accomplished by recording in non-volatile memory or by any other suitable technique available for a given implant. With the completion of this step 120, RV-LV cardiac resynchronization has been successfully completed.

At step 125, a technician, physician, or other operator will program a range for paced rate suitable for the given patient. As with step 105, this programming of suitable range may be accomplished in any manner compatible with a given implant. In accord with method 100, the patient's Heart Rate (HR) will be varied through the paced rate range as shown in step 130. During the varying of HR, the patient's hemodynamic performance will again be recorded using suitable recording technique. Once the HR has been varied through the entire programmed paced rate range, the optimal HR will then be determined at step 135. As before, this determination may be either manual, semi-automatic, or automatic. Once the optimal HR is determined, then the pacer will be set to that optimal HR, as illustrated by step 135. Most frequently, this setting will be stored in non-volatile memory for access by the implant microprocessor or microcontroller.

At step 145 illustrated in FIG. 1, a decision must be made. At this step, the system must determine whether normalized atrial rhythm is present. If it is not, then preferred method 100 will be completed. Control will then be returned to the normal implant operations, but using the optimal values for RV-LV delay and HR determined as a result of method 100.

If, instead, normalized atrial rhythm is present, then optimal Atrial-Ventricular (AV) delays will be determined through steps 150–165. In step 150, the technician, physician or other operator will program a suitable AV delay range for the given patient. By now it should be apparent to those reasonably skilled in the art that although a linear flow chart is illustrated, some of the steps may not be required to be performed in the order illustrated. More particularly, but only for exemplary purposes and not solely limited thereto, each of the range programming steps 105, 125, and 150 may be accomplished together, for example at the very beginning of method 100, at the time of step 105 as illustrated in FIG. 1. Alternatively, the programming may be saved for the gathering of additional data, and ranges selected with the benefit of the information gathered in prior steps of method 100. Those skilled in the art will determine exact sequences of the various steps of the present method, upon a review of the present disclosure and in conjunction with the needs of a particular implant or patient. In step 155, AV delay(s) are varied through the programmed range. As may be apparent, if the implant is only capable of right AV delay, then only a single AV delay will be varied. However, if both right and left AV delays may be varied, then this capability will most preferably be offered to the operator. As with steps 110 and 130, as the AV delay is varied, the patient's hemodynamic performance will be monitored through suitable physiological parameter(s) and recorded. Next, and similar to steps 115 and 135, step 160 involves determining the optimal AV delay(s). This may be automatically accomplished, or instead the data may be presented to an operator for selection of preferred delays. Once selected, the implant will be set to the selected optimal AV delay in step 165.

After completion of step 165, the preferred method 100 will be completed, as illustrated by step 170. Control will then be returned to the normal implant operations, using the optimal values for RV-LV delay, HR, and AV delay determined as a result of method 100.

Figure 2:
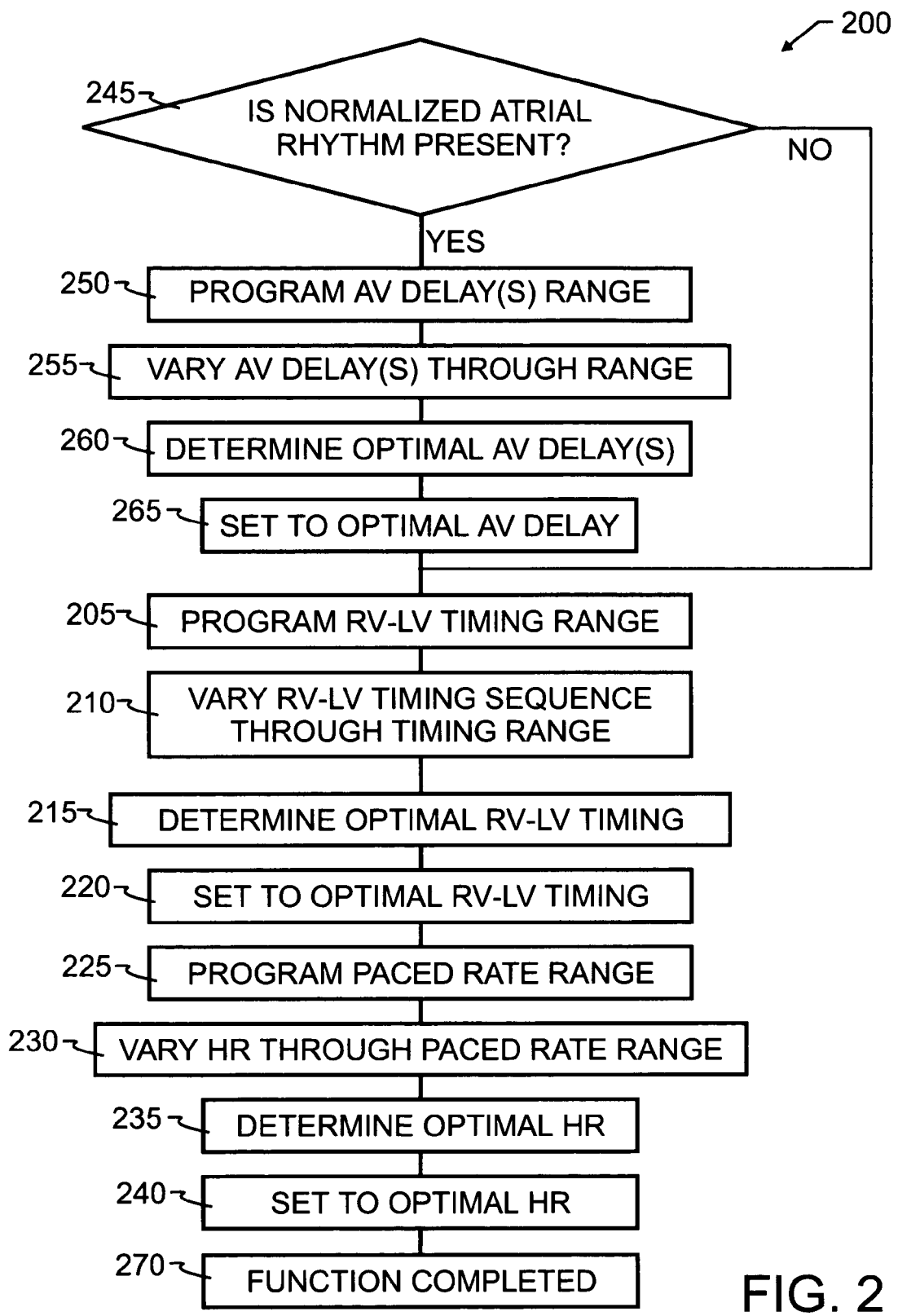
FIG. 2 illustrates a second preferred method of hemodynamic optimization for biventricular implants, designed in accord with the teachings of the present invention, by flow chart.

FIG. 2 illustrates a second preferred method 200. Numbering has been designated to correspond to associated steps of FIG. 1, where the ones and tens digits match those of like steps in FIG. 1. The leading (hundreds) digit is a two, specifically reflecting that the step is one from method 200. As will be apparent upon a review of method 200, the steps match those of method 100. However, the order has been changed in method 200, to detect whether normalized atrial rhythm is present at step 245 before any other step. In method 100, this determination at step 145 was made subsequent to setting optimal RV-LV timing and HR. From this FIG. 2 then, those reasonably skilled in the art will recognize that the selection of optimizing a particular delay or heart rate may be made in any suitable sequence with respect to other delays and heart rate. Furthermore, while preferred methods 100 and 200 utilize only single variable optimization, it will also be apparent that where necessary or appropriate to justify the additional complexity that will be required, the present invention will similarly permit the variation of more than one parameter through a range, with the ultimate selection of optimal value being made dependent upon each or all variables to optimize hemodynamic performance. Said another way, it is conceived that RV-LV delay and AV delay, for example, may both be varied, simultaneously, through the entire matrix of all possible combinations of each, with the optimal value for both then being determined and set. While this alternative approach may help to eliminate interdependence of variables, it will also be recognized that this alternative approach is more complex to implement and will require substantially more time to execute.

As aforementioned, most preferably the implant will be capable of automatically recording hemodynamic information and adjusting intervals, in order to optimize hemodynamics. Also preferably, the automatic adjusting feature can be selectively programmed on or off using the device programmer. This device programmer may be coupled through radio link or other electromagnetic wave, directly coupled, or otherwise coupled to the implant using known techniques. By selectively permitting automatic recording and adjusting, the device may be initially manually programmed to suit the needs of a particular patient, such as the selection and setting of ranges as in steps 105, 125, and 150. Where possible, the device may then be tested and adjusted in vivo. Once preferred operation is confirmed, the implant may then be set to automatic operation. The implant may, in one conceived embodiment, also be set to periodically automatically determine optimal values.

With appropriate interface, medical personnel may additionally be provided with the necessary coupling to read the various data stored within the implant (either remotely or directly) which may, for exemplary purposes, include physiological parameters obtained with varying values for the chosen timing and HR values and may also include the optimal values in use at the time. In the event of an emergency medical situation, such data may prove to be very useful and important.

In accord with the teachings of the present invention, the preferred methods will find the patient's best timing sequences to achieve optimal circulation, and will thereby improve contractility, the patient's left ventricular ejection fraction, and their symptoms, including overall quality of life. This is achieved by cycling through full ranges of potentially suitable values, and, upon completion of the cycle, determining and setting the optimum value.

Those skilled in the art will recognize that the teachings of the present invention may be applied to the entire method as illustrated in FIGS. 1 and 2, but that individual optimizations of one or more of the delays, timings and rates may also be selected, absent the remaining delays, timings and rates illustrated in those figures, where appropriate for a given application. The decision for which parameters to optimize, including those disclosed herein and others that are or may become known in the art, will remain with a suitably skilled designer fully cognizant of the present disclosure.

While the foregoing details what is felt to be the preferred embodiment of the invention, no material limitations to the scope of the claimed invention are intended. Further, features and design alternatives that would be obvious to one of ordinary skill in the art are considered to be incorporated herein. The scope of the invention is set forth and particularly described in the claims herein below.

I claim:

1. A multi-mode system for monitoring a patient and treating a malfunctioning heart of the patient selectively in automatic and semiautomatic modes, the system comprising: means for deriving at least one physiological signal representative of a hemodynamic status of the patient, output means for providing at least one heart-malfunction-corrective output, range controlling means for limiting upper and lower bounds for said at least one heart-malfunction-corrective output, scanning means for varying delivery of said at least one heart-malfunction-corrective output, monitoring means for recording said at least one physiologic signal responsive to changes in delivery by said scanning means, and mode selection means operable by a human operator for enabling said means for providing the at least one heart-malfunction-corrective output to operate selectively in an automatic mode independent of said human operator and in semiautomatic mode requiring confirmation by said human operator, whereby at least one malfunction of the heart may be treated selectively in automatic and semiautomatic modes, wherein said monitoring means for recording said at least one physiologic signal responsive to changes in delivery by said scanning means further comprises displaying said at least one physiologic signal responsive to changes in delivery by said scanning means.

2. A multi-mode system for monitoring a patient and treating a malfunctioning heart of the patient according to claim 1, wherein said at least one heart-malfunction-corrective output further comprises an electrical signal to said patient's heart.

3. A multi-mode system for monitoring a patient and treating a malfunctioning heart of the patient according to claim 1, wherein said heart-malfunction-corrective output further comprises atrioventricular (AV) delay.

4. A multi-mode system for monitoring a patient and treating a malfunctioning heart of the patient according to claim 1, wherein said heart-malfunction-corrective output further comprises right ventricular (RV) to left ventricular (LV) timing.

5. A multi-mode system for monitoring a patient and treating a malfunctioning heart of the patient according to claim 1, wherein said heart-malfunction-corrective output further comprises heart rate adjustment.

6. A multi-mode system for monitoring a patient and treating a malfunctioning heart of the patient according to claim 1, wherein said heart-malfunction-corrective output further comprises atrioventricular (AV) delay, right ventricular (RV) to left ventricular (LV) timing, and heart rate adjustment.

7. A multi-mode system for monitoring a patient and treating a malfunctioning heart of the patient accord to claim 1, wherein said scanning means for varying delivery of said at least one heart-malfunction-corrective output is responsive to said range controlling means and restrained thereby within said upper and lower range bounds.

8. The multi-mode system for monitoring a patient and treating a malfunctioning heart of the patient of claim 1, wherein said displaying further comprises graphing.

9. A system for monitoring a patient and treating the malfunctioning heart of the patient through electrical signals generating by a biventricular pacemaker and coupled to said patient's heart, comprising: means for deriving at least one physiologic signal representative of said patient's hemodynamic status; means for varying at least one of atrioventricular (AV) delay, right ventricular (RV) to left ventricular (LV) timing and heart rate of said electrical signal; a range of values for each said at least one of atrioventricular (AV) delay, right ventricular (RV) to left ventricular (LV) timing and heart; a feedback loop which initiates said varying means to vary said at least one of said series of AV delay, RV-LV timing and heart rate of said electrical signals varied through said range of values; a means to apply said electrical signals varied through said range of values to the patient's heart; recording means to measure said varied electrical signals and said physiologic signal responsive ti said varied electrical signals; means to determine an optimum value from said range of values responsive to said recording means and said feedback loop; and means to select at least one of an optimal AV delay, optimal RV-LV limiting sequence and an optimal pacing rate to secure an optimized timing sequence for said patient wherein said recording means to measure said varied electrical signals and said physiologic signal responsive to said varied electrical signals further comprises a means to graph said physiologic signal with respect to said varied electrical signals.

10. A system for monitoring a patient and treating the malfunctioning heart of the patient by a biventricular pacemaker according to claim 9, wherein said range of values are programmable.

11. The system for monitoring a patient and treating the malfunctioning heart of the patient by a biventricular pacemaker of claim 10, wherein said range of values are preselected by a human operator.

12. A system for monitoring a patient and treating the malfunctioning heart of the patient by a biventricular pacemaker according to claim 9, wherein said means to select at least one of an optimal AV delay, optimal RV-LV timing sequence and an optimal pacing rate further comprises a human operator manually selecting.

13. A system for monitoring a patient and treating the malfunctioning heart of the patient by a biventricular pacemaker according to claim 9, wherein said means to select at least one of an optimal AV delay, optimal RV-LV timing sequence and an optimal pacing rate further comprises said biventricular pacemaker automatically selecting.

14. A system for monitoring a patient and treating the malfunctioning heart of the patient by a biventricular pacemaker according to claim 9, wherein said feedback loop initiates said varying means to vary said atrioventricular (AV) delay, said right ventricular (RV) to left ventricular (LV) timing and said heart rate.

15. A system for monitoring a patient and treating the malfunctioning heart of the patient by a biventricular pacemaker claim 9, wherein said feedback loop initiates said varying means to vary said atrioventricular (AV) delay.

16. A system for monitoring a patient and treating the malfunctioning heart of the patient by a biventricular pacemaker according to claim 9, wherein said feedback loop initiates said varying means to vary said right ventricular (RV) to left ventricular (LV) timing.

17. A system for monitoring a patient and treating the malfunctioning heart of the patient by a biventricular pacemaker according to claim 9, wherein said feedback loop initiates said varying means to vary said heart rate.

18. A system for monitoring a patient and treating the malfunctioning heart of the patient by a biventricular pacemaker according to claim 9, wherein said feedback loop initiates said varying means to vary said right ventricular (RV) to left ventricular (LV) timing and said heart rate.

19. A system for monitoring a patient and treating the malfunctioning heart of the patient by a biventricular pacemaker according to claim 9, further comprising means for automatically recording hemodynamic information and adjusting intervals to optimize hemodynamics without third party intervention, to automatically optimize said patient's clinical hemodynamic status.

20. The system for monitoring a patient and treating the malfunctioning heart of the patient by a biventricular pacemaker of claim 19, wherein said automatic recording means is selectively controlled to be alternatively operative and inoperative, to control manual or automatic intervention.

21. A system for monitoring a patient and treating the malfunctioning heart of the patient through electrical signals generating by a biventricular pacemaker and coupled to patient's heart, comprising: means for deriving at least one physiologic signal representative of said patient's hemodynamic status; means for varying each of a left artioventricular (AV) delay, a right atrioventricular (AV) delay, a right ventricular (RV) to left ventricular (LV) timing, and a heart rate using said electrical signals; a feedback loop which initiates said varying means to vary at least one of said left and right AV delays, RV-LV timing and heart rate of said electrical signals through said range of values; a means to apply said electrical signals varied through said range of values to the patient's heart; recording means to measure said electrical signals and said physiologic signal responsive to said varied electrical signals; means to determine an optimum valued from said range of values responsive to said recording means and said feedback loop; and means to select at one of an optimal pacing rate to secure an optimal right AV delay, an optimal RV-LV timing sequence and an optimal pacing rate to secure an optimized timing sequence for said patient wherein said recording means to measure said varied electrical signals and said physiologic signal responsive to said varied electrical signals further comprises a means to graph said physiologic signal with respect to said varied electrical signals.

22. A system for monitoring a patient and treating the malfunctioning heart of the patient by a biventricular pacemaker according to claim 21, wherein said range of values are programmable.

23. A system for monitoring a patent and treating the malfunctioning heart of the patient by a biventricular pacemaker according to claim 21, wherein said range of values are preselected by a human operator.

24. A system for monitoring a patient and treating the malfunctioning heart of the patient by a biventricular pacemaker according to claim 21, wherein said means to select at least one of an optimal left AV delay, an optimal right AV delay, and optimal RV-LV timing sequence and an optimal pacing rate further comprises a human operator manually selecting.

25. A system for monitoring a patient and treating the malfunctioning heart of the patient by a biventricular pacemaker according to claim 21, wherein said means to select at least one of an optimal left AV delay, an optimal right AV delay, an optimal RV-LV timing sequence and an optimal pacing rate further comprises said biventricular pacemaker automatically selecting.

26. A system for monitoring a patient and treating the malfunctioning heart of the patient by a biventricular pacemaker according to claim 21, wherein said feedback loop initiates said varying means to vary said left atrioventricular (AV) delay, said right atrioventricular (AV) delay, and right ventricular (RV) to left ventricular (LV) timing and said heart rate.

27. A system for monitoring a patient and treating the malfunctioning heart of the patient by a biventricular pacemaker according to claim 21, wherein said feedback loop initiates said varying means to vary said left atrioventricular (AV) delay.

28. A system for monitoring a patient and treating the malfunctioning heart of the patient by a biventricular pacemaker according to claim 21, wherein said feedback loop initiates said varying means to vary said right atrioventricular (AV) delay.

29. A system for monitoring a patient and treating the malfunctioning heart of the patient by a biventricular pacemaker according to claim 21, wherein said feedback loop initiates said varying means to vary said right ventricular (RV) to left ventricular (LV) timing.

30. A system for monitoring a patient and treating the malfunctioning heart of the patient by a biventricular pacemaker according to claim 21, wherein said feedback loop initiates said varying means to vary said heart rate.

31. A system for monitoring a patient and treating the malfunctioning heart of the patient by a biventricular pacemaker according to claim 21, wherein said feedback loop initiates said varying means to vary said right ventricular (RV) to left ventricular (LV) timing and said heart rate.

32. A system for monitoring a patient and treating the malfunctioning heart of the patient by a biventricular pacemaker according to claim 21, further comprising means for automatically recording hemodynamic information and adjusting intervals to optimize hemodynamics without third party intervention, to automatically optimize said patient's clinical hemodynamic status.

33. The system for monitoring a patient and treating the malfunctioning heart of the patient by a biventricular pacemaker of claim 32, wherein said automatic recording means is selectively controlled to be alternatively operative and inoperative, to control manual or automatic intervention.

* * * * *